«12» United States Patent
Kuech et al.

(10) Patent No.: US 8,369,915 B2
(45) Date of Patent: Feb. 5, 2013

(54) INTEGRATED MINIATURIZED FIBER OPTIC PROBE

(75) Inventors: Thomas F. Kuech, Madison, WI (US); Nirmala Ramanujam, Durham, NC (US); Leon McCaughan, Madison, WI (US)

(73) Assignees: Wisconsin Alumni Research Foundation, Madison, WI (US); Duke University, Durham, NC (US)

( * ) Notice: Subject to any disclaimer, the term of this patent is extended or adjusted under 35 U.S.C. 154(b) by 583 days.

(21) Appl. No.: 12/613,715

(22) Filed: Nov. 6, 2009

(65) Prior Publication Data

US 2011/0112388 A1 May 12, 2011

(51) Int. Cl.
*A61B 5/1459* (2006.01)
(52) U.S. Cl. ........................................................ 600/341
(58) Field of Classification Search .................. 600/341
See application file for complete search history.

(56) References Cited

U.S. PATENT DOCUMENTS

| 5,138,145 | A | * | 8/1992 | Nakamura et al. ......... 250/208.1 |
| 5,349,954 | A | | 9/1994 | Tiemann et al. |
| 5,821,171 | A | * | 10/1998 | Hong et al. .................... 438/767 |
| 6,104,371 | A | | 8/2000 | Wang et al. |
| 6,215,801 | B1 | * | 4/2001 | Ackerman et al. .............. 372/32 |
| 7,149,562 | B2 | * | 12/2006 | Walker et al. ................. 600/339 |
| 2005/0203419 | A1 | | 9/2005 | Ramanujam et al. |
| 2006/0045431 | A1 | * | 3/2006 | Boisvert et al. ................ 385/88 |
| 2007/0085016 | A1 | * | 4/2007 | Schulz ..................... 250/370.11 |
| 2007/0257186 | A1 | * | 11/2007 | Delcher et al. ............. 250/208.2 |
| 2008/0181557 | A1 | * | 7/2008 | Wang et al. ..................... 385/14 |
| 2011/0112388 | A1 | * | 5/2011 | Kuech et al. .................. 600/341 |

OTHER PUBLICATIONS

Utzinger, U., "Fiber optic probes for biomedical optical spectroscopy", Journal of Biomedical Optics 8(1) 121-147m Jan. 2003.

* cited by examiner

*Primary Examiner* — W.B. Perkey
(74) *Attorney, Agent, or Firm* — Bell & Manning, LLC

(57) ABSTRACT

A fiber optic probe having one or more photodetectors bound thereto is provided. By directly integrating thin, flexible photodetectors with an optical fiber, the probes provide a compact structure that increases throughput and decreases cost, making it practical for a clinical use. In some embodiments, the fiber optic probes are small enough for insertion into the shaft of a needle, such as a biopsy needle.

20 Claims, 8 Drawing Sheets (a)

(b)

INTEGRATED MINIATURIZED FIBER OPTIC PROBE

STATEMENT REGARDING FEDERALLY SPONSORED RESEARCH OR DEVELOPMENT

This invention was made with United States government support awarded by the following agencies: ARMY/MRMC W81XWH-05-1-0363. The United States government has certain rights in this invention.

FIELD OF THE INVENTION

The present invention relates to spectrometry devices. More specifically, this invention relates to optical fibers having photodetectors bound thereto.

BACKGROUND

The use of light-based diagnostics is growing due to their non-intrusive behavior, and potentially rapid implementation with existing techniques. One such diagnostic technique, diffuse reflectance spectroscopy, is sensitive to the absorption and scattering properties of biological molecules in tissue and thus can be used as a tool for quantitative tissue biology in vivo. One major absorber of light in tissue in the visible range is hemoglobin, which shows distinctive, wavelength-dependent absorbance characteristics depending on its concentration and oxygenation. Light scattering in tissue is sensitive to the size, density, and refractive indices of cellular structures such as nuclei and mitochondria. Thus, diffuse reflectance spectroscopy (absorption and scattering) of tissues can quantify changes in oxygenation, blood volume and alterations in cellular density and morphology. Implementation of such detection strategies, however, is limited by the bulky and expensive nature of existing light sources and detectors.

BRIEF SUMMARY

Fiber optic probes, methods for using the fiber optic probes in spectroscopic applications and methods for making the fiber optic probes are provided.

One aspect of the invention provides a fiber optic probe comprising an optical fiber, at least one photodetector having a device layer bonded to and conforming to the optical fiber and an electrically conductive lead in electrical communication with the at least one photodetector. The fiber optic probe can, optionally, further comprise a layer of electrically conductive material disposed between the optical fiber and the at least one photodetector. In addition, the fiber optic probe can include a layer of dielectric material coating a portion of the external surface of the photodetector.

The fiber optic probes make local detection of light possible by placing the photodetector(s) very close to the light-emitting locations along the optical fiber. In some embodiments, a photodetector is located no more than 10 mm from the distal end of the optical fiber. The optical fiber can be configured to emit light from its distal end and/or from at least one additional location along its length and/or around its circumference. In such embodiments, the probe can include at least one additional photodetector in the vicinity of each additional light-emitting location.

In some embodiments, the optical fibers desirably have sufficiently small diameters to allow them to be inserted in the shaft of a needle, such as a biopsy needle.

Another aspect of the invention provides methods for using the fiber optic probes in spectroscopic applications. One such method includes the steps of placing the optical fiber of a fiber optic probe in close proximity to a sample, directing light from the optical fiber onto the sample and detecting return light from the sample. In some embodiments of the method, the sample comprises a biological tissue. The method can be carried out by inserting the optical fiber into a biopsy needle and inserting the optical fiber into the sample.

In one application, the return light can be used to measure the wavelength-dependent absorbance characteristics of hemoglobin in the biological tissue sample in vivo.

DETAILED DESCRIPTION

A fiber optic probe having one or more photodetectors bound thereto is provided. By directly integrating thin, flexible photodetectors with an optical fiber, the probes provide a compact structure that increases throughput and decreases cost, making it practical for a clinical use. In some embodiments the fiber optic probes are small enough for insertion into the shaft of a needle, such as a biopsy needle.

The fiber optic probes can be used for in vitro and in vivo studies of samples, including biological samples, such as tissues and liquid samples. For example, the fiber optic probes can be used for in vivo sensing of the presence of biochemical and morphological changes associated with normal and abnormal tissues. In various embodiments, the optical probes can be designed for use in fluorescence spectroscopy, reflectance spectroscopy, Raman spectroscopy or a combination thereof. For example, the optical probes can be used to study the absorption and scattering characteristics of a biological sample to monitor oxy- and deoxygenated hemoglobin, water, beta-carotene, melanin and/or bilirubin in a tissue sample and to derive information about total blood concentration and average blood oxygenation therefrom. The fiber optic probes also can be used in reflectance spectroscopy to decimate between normal and abnormal tissues, such as cancerous tissues. Alternatively, the fiber optic probes can be used in fluorescence spectroscopy studies of samples containing chromophores. In addition, the fiber optic probes can be used in NIR Raman scattering studies to perform histochemical analysis on a sample, or to study hemoglobin, water and lipids in tissue, such as breast tissue and to distinguish healthy breast tissue from cancerous breast tissue.

In a basic embodiment of a method for using a fiber optic probe, the optical fiber is placed in close proximity to a sample of interest, such as a biological tissue or liquid. Incident light emitted from one or more light-emitting locations on the optical fiber is directed onto the sample and return light is detected by one or more photodetectors bonded to the optical fiber. Return light can be either light that is scattered by the sample, or light that fluoresces from the sample, as in the case of fluorescence spectroscopy. For the purposes of this disclosure, an optical fiber is in close proximity to a sample of interested if it is sufficiently close to direct light onto the sample with sufficient intensity, that the resulting reflected or fluorescent light from the sample is detectable by one or more photodetectors bonded to the optical fiber. This includes optical fibers that are in direct contact with the sample of interest.

Figure 1:
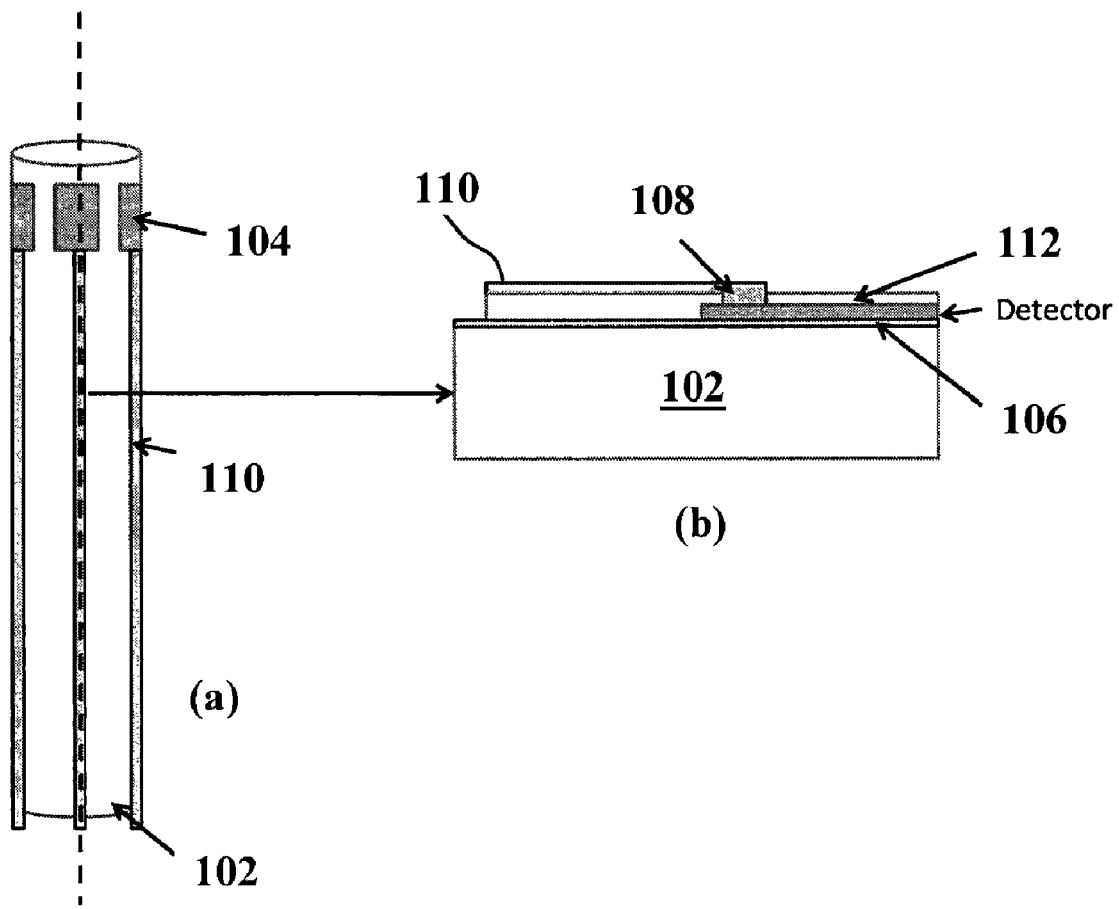
FIG. 1 shows a schematic illustration of an embodiment of a fiber optic probe.

A schematic illustration of a basic embodiment of a fiber optic probe is illustrated in FIG. 1(a). A partial cross-sectional view of the fiber optic probe, taken along the dashed list in FIG. 1(a), is shown in FIG. 1(b). The fiber optic probe includes an optical fiber 102 and a plurality of flexible photodetectors 104 disposed around and conforming to the circumference of the optical fiber. In the embodiment of FIG. 1, a layer of electrically conductive material 106 coats at least a portion of the external surface of the optical fiber. This layer of electrically conductive material 106 provides a back contact for the flexible photodetectors. Each of the photodetectors includes an electrically conductive contact 108 and an electrically conductive lead 110 in electrical communication with the photodetector. Optionally, a layer of dielectric material 112 may be disposed over the photodetectors and/or between the electrically conductive leads 110 and the back contact material 106 to provide electrical isolation.

A basic embodiment of the optical fiber will include an inner core layer, an outer cladding layer disposed around the inner core layer and, optionally, an outer protective jacket. Suitable materials for the core layer include glass, plastic and high-grade fused silica. The cladding layer is typically a doped material having a lower index of refraction than the core layer material. The optical fiber desirably has dimensions that enable it to be inserted into the shaft of a needle, such as a biopsy needle. For example, in some embodiments, the optical fiber has a diameter of 1 mm or less. This includes embodiments in which the optical fiber has a diameter of 0.5 mm or less and further includes embodiments in which the optical fiber has a diameter of 0.5 mm or less. The optical fiber can be dimensioned to provide a single mode or a multimode waveguide. Thus, in some embodiments, the optical fiber has a core diameter of about 10 to 100 microns. The length of the optical fiber will depend on the location of the sample to be probed and on the length of any needle into which it is to be inserted. By way of illustration only, in some embodiments, the optical fiber has a length on the order of tens of mm (e.g., $\geq$10 mm) to tens of cm (e.g., $\geq$10 cm), although lengths outside of this range can also be employed.

The optical fiber can be designed to emit light from one or more locations along its length. For example, the optical fiber can be designed to emit light from its distal end (i.e., the end adapted for insertion into a sample). The light can be emitted from the distal end of the optical fiber in a direction parallel to the longitudinal axis of the optical fiber. Alternatively, the optical fiber can be configured to emit light from its distal end at an oblique angle with respect to the longitudinal axis of the fiber. In some embodiments, the distal end of the optical fiber can be cut at an oblique angle to emit light at angles of, for example, 5° to 85° (e.g., 45°) with respect to the longitudinal axis of the optical fiber. Alternatively, the distal end of the optical fiber can take the form of an inverted cone or hemisphere, such that the fiber is adapted to emit light around the entire circumference) (360° of its distal end. In some embodiments, a diffuser tip can be disposed at the distal end of the optical fiber in order to provide diffuse, homogeneous illumination from the distal end of the fiber about its central longitudinal axis. Examples of optical fibers having beveled ends, hemispherical ends and diffuser tips are described in Utzinger et al., J. Biomedical Optics, 8(1), 121-147 (2003).

Figure 2:
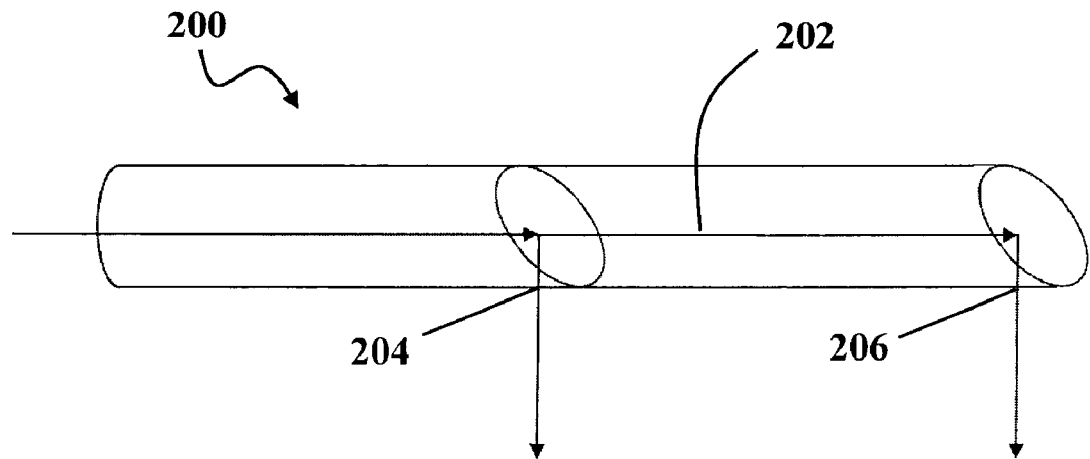
FIG. 2(a) shows a schematic diagram of an optical fiber having two light-emitting locations.
FIG. 2(b) shows a cross-sectional view of the optical fiber of FIG. 2(a) having two photodetectors mounted thereon.
Figure 2:
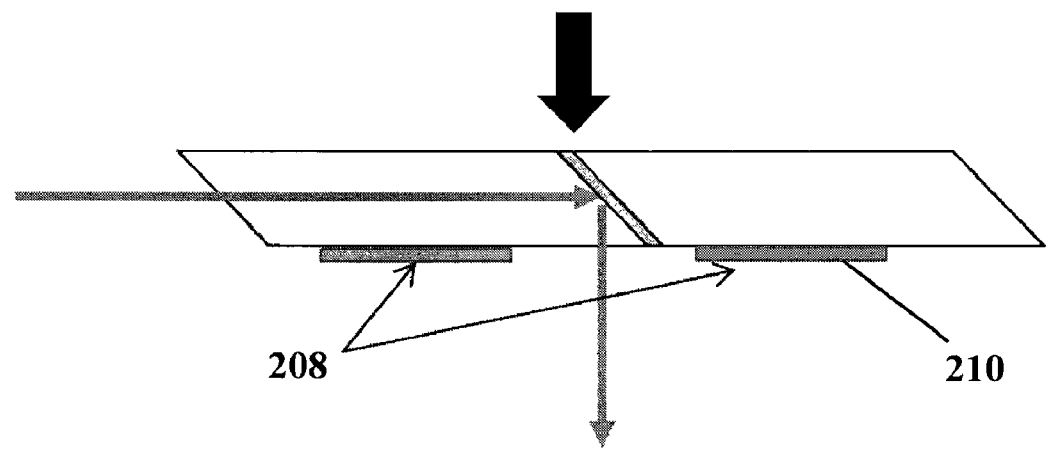

As an alternative to (or in addition to) emitting light from its distal end, the optical fiber may be configured to emit light through the side-wall of the fiber at one or more locations along its length and/or one or more locations around its circumference. For example, the optical fiber can be adapted to emit light at a plurality of locations along its length. In such embodiments, each light-emitting location can be (but need not to be) aligned along a single longitudinal axis running along the length of the optical fiber. Similarly, the optical fiber can be adapted to emit light at a plurality of locations around its circumference. Methods for adapting an optical fiber to emit light at various angles through the side wall of the fiber are known. For example, angled cuts or notches can be cut into the side wall of the optical fiber, such cuts or notches, which may be coated with a reflective coating, can act as internal mirrors, reflecting light out of the side of the optical fiber. Examples of internal mirrors in an optical fiber are described in U.S. Pat. No. 6,104,371. FIG. 2(a) provides a schematic diagram an optical fiber 200 that emits light at a 45 angle with respect to the central longitudinal axis of the fiber 202 at two different light-emitting locations 204, 206.

Figure 5A:
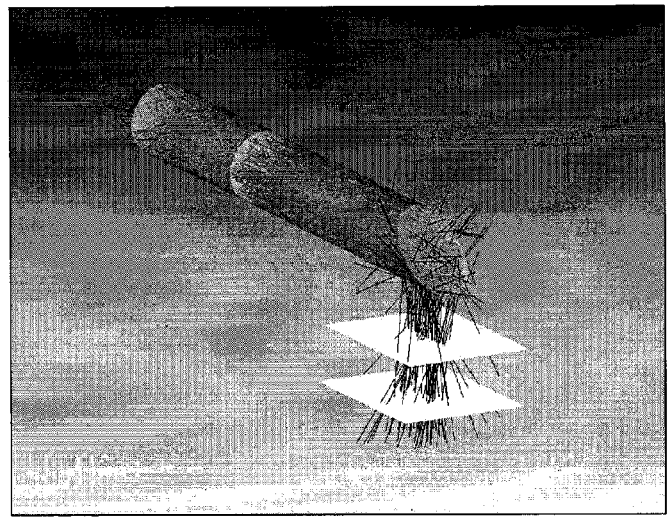
FIG. 5 shows: (a) GRIN rod deflection geometry; and (b) Light intensity profile of the focused light beam at −0.75 mm below the GRIN rod. For each system, 500 nm wavelength of light at 1 W was used.
Figure 5B:
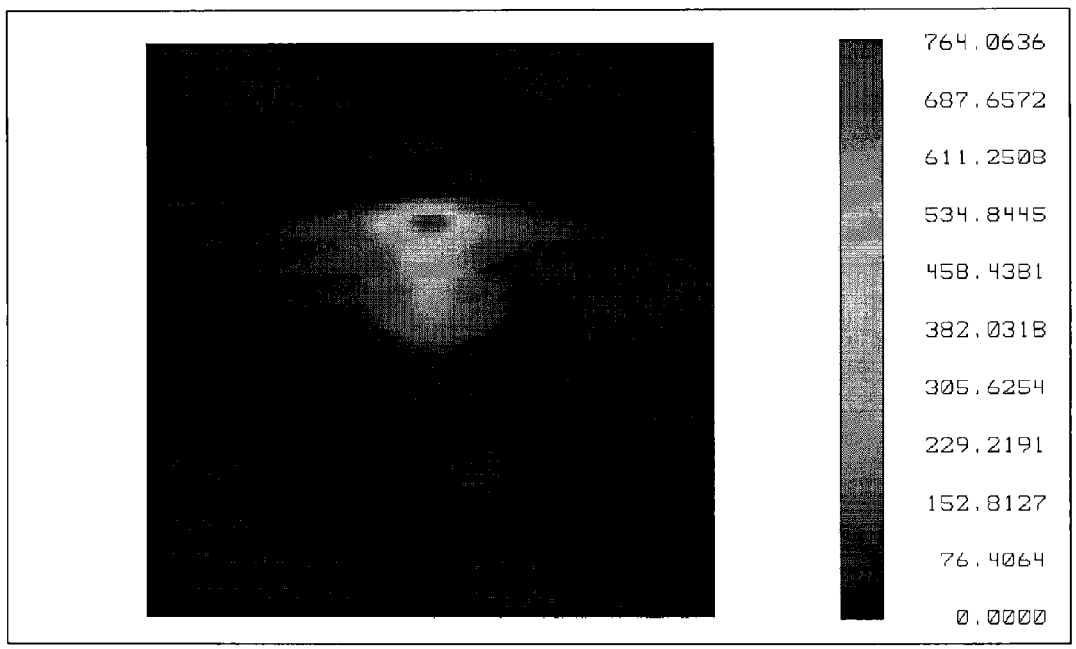

In some embodiments, light is emitted at a right angle with respect to the longitudinal axis of the optical fiber. To achieve right angle deflection, the light exiting the fiber should first be collimated and then be allowed to fall on a surface cut at a 45 degree angle. Under many circumstances, a 45 degree angled surface is sufficient to produce total internal reflection. (If necessary, this angled surface could be coated to enhance its reflectivity.) One solution is to use a ¼ pitch graded index (GRIN) lens, attached to the distal end of the optical fiber, to provide a parallel (collimated) beam of light. This collimated beam then can be allowed to fall on a 45 angle-cut surface cut across the distal end of the GRIN lens. FIG. 5(a) shows such a structure, and FIG. 5(b) is a display of the light intensity profile perpendicular to the axis of the fiber-GRIN lens combination. The diameter of the GRIN rod in this example is 0.5 mm and a length of 3.45 mm. The optical fiber input is modeled as a point source since the diameter of the fiber optic core (~10-100 μm) is typically much smaller than the diameter of the GRIN rod. After deflection by the 45°surface, the combination of the cylindrical boundary and the graded index provides some focusing of the light, both parallel to and perpendicular to the axis of the GRIN rod.

Figure 6:
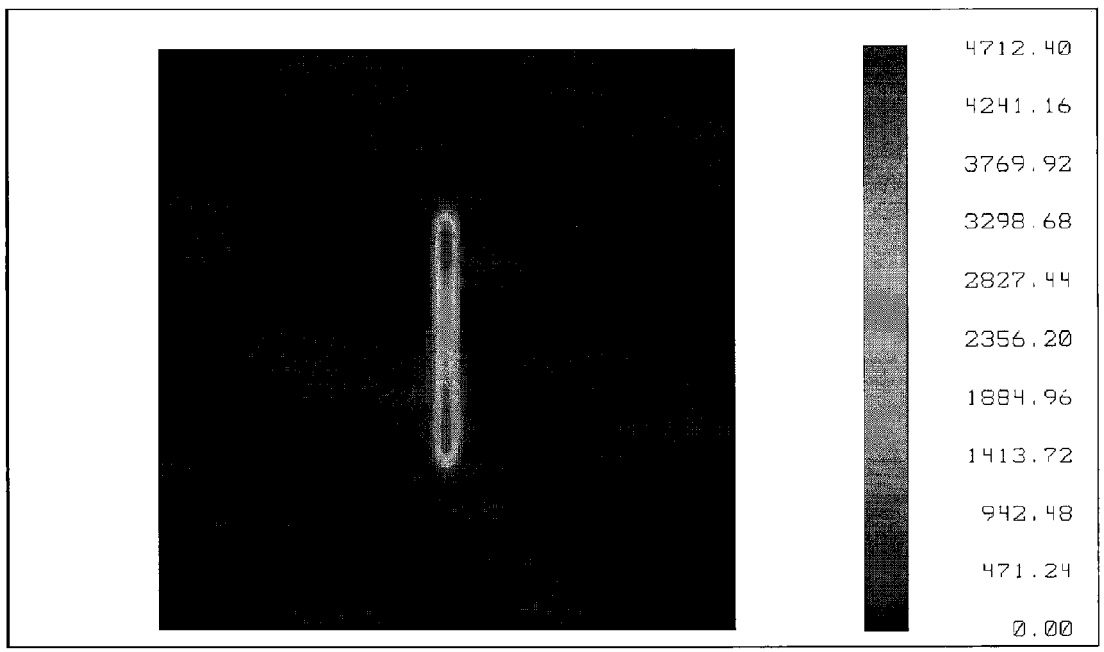
FIG. 6 shows a detector view of a focused light beam at −0.35 mm below a cylindrical rod.

If a ¼ pitch GRIN lens (¼ pitch at 0.5 mm diameter, 1.15 mm length) is used to collimate the light from the fiber, but a separate solid cylinder of glass of uniform index (e.g., BK7 glass 0.5 mm dia., 2 mm long), with a 45 degree angle cut is used to deflect the light, the focusing by the glass rod occurs parallel to the axis of the rod. In such an embodiment, the absence of the cylindrically graded index eliminates any focusing perpendicular to the rod, as shown in FIG. 6. This geometry would be advantageous to sweeping out a larger scan area by rotating the optical fiber.

Figure 7:
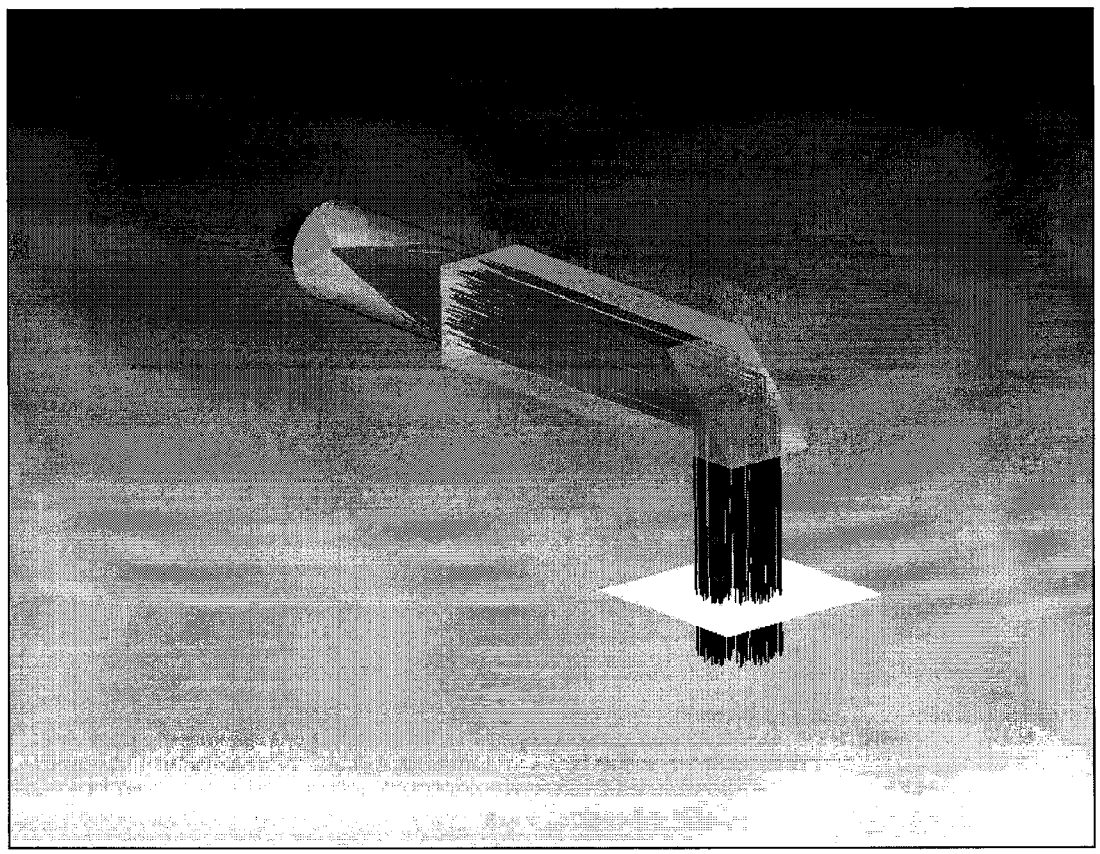
FIG. 7 shows a collimated light then entering an angled cut glass rod with a rectangular cross section.
Figure 8:
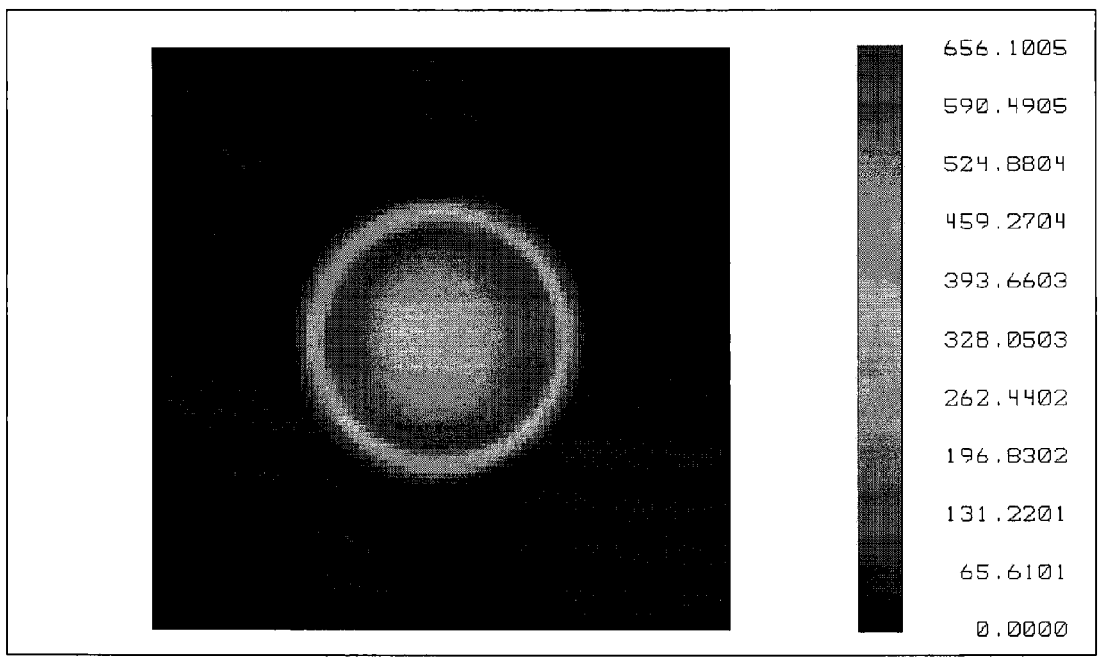
FIG. 8 shows the profile of a collimated beam, where the red are more densely packed rays and the blue are lower densely packed rays.

To produce a 90 degree deflection but eliminate all focusing, a glass rod with a rectangular cross section can be used in place of the cylindrical geometry as a deflecting element. As before, a GRIN lens can be used first to collimate the light exiting the fiber. The collimated light then enters an angled cut glass rod with a rectangular cross section (FIG. 7). As before, the collimated rays are totally internally reflected 90° to the incident rays. The reflected rays pass through the glass at normal incidence, and are therefore not refracted. FIG. 8 shows the profile of the collimated beam, where the red are more densely packed rays and the blue is lower densely packed rays. Such an arrangement can provide a more uniform illumination scheme than either of the other constructs above. The throughput of the rectangular glass deflector in this example is 90.1%.

The probes are desirably designed such that the wall of the needle shaft does not significantly block, or otherwise interfere with, the emitted or reflected light. Thus, in some embodiments, the shaft of the needle can include apertures or transparent windows positioned to allow emitted and reflected light to pass. In some embodiments, as in the case where radiation is emitted and detected at or near the distal end of the probe, the distal end of the optical fiber, including the photodetector(s) in the vicinity of the distal end of the fiber, can extend beyond the needle shaft and into a sample. This can be accomplished by inserting the needle into the sample and then retracting the shaft such that the distal end of the optical fiber extends beyond the distal end of the shaft and into the sample.

The proximal end of the optical fiber is in optical communication with a light source. A wide variety of optical fibers currently exist optimized for a variety of spectral bands from the infrared (IR), including near infrared (NIR), through the (UV). The selected light source will depend upon the intended application for the fiber optic probe. By way of illustration only, suitable light sources can emit radiation in the wavelength range of about 200 mm to about 3000 nm and include, but are not limited to, arc lamps, light emitting diodes and lasers. Other optional components that can be combined with the light source include filters, mirrors and optical elements used to filter, focus and/or direct the light from the source into the optical fiber.

Optionally, the fiber can be coated with an electrically conductive material to provide a back electrode for the photodetector(s). This coating can be a continuous or discontinuous coating on the external surface of the optical fiber. For example, the coating can comprise an electrically conductive material, such as indium tin oxide (ITO) that is transparent at the wavelengths of interest disposed between the external surface of the optical fiber and one or more photodiodes. Alternatively, the coating can be a thin metal coating with openings having dimensions and locations suitable to allow the passage of emitted and reflected light.

The device layers of the one or more photodetectors bonded to the optical fiber should be sufficiently thin and flexible to allow them to conform to the shape of the outer surface of the optical fiber, as illustrated in FIG. 1. This thin layer structure allows the device layers of the photodetectors to be bonded onto the curved surface of the optical fiber such that the radius of curvature is much greater than the thickness of the device layers. However, the device layers should be sufficiently thick to allow for adsorption of the wavelengths of interest in the device layers. For many device layer materials, including, direct bandgap semiconductors, wavelengths of interest can be adsorbed within a very thin device layer. Thus, in some embodiments, the device layers will have a thickness of no greater than about 10 μm. This includes embodiments in which the device layers have a thickness no greater than about 6 μm and further includes embodiments in which the device layers have a thickness of no greater than about 3 μm.

Specific examples of suitable photodetectors include thin film semiconductor photodetectors having direct bandgap semiconductor-based device layers. These include device layers based on GaAs, InP, GaN and materials lattice matched or pseudomorphically grown on these substrate materials. The GaAs-based materials are useful in the wavelength range of 400-850 nm, while the InP-based materials are useful at longer wavelengths and GaN-based device layers are useful for UV applications.

Each of the one or more photodetectors can be bound to the optical fiber in the vicinity of at least one light-emitting location. For the purposes of this disclosure, a photodetector is "in the vicinity of" a light-emitting location if that photodetector is sufficiently close to that light-emitting location to detect light emitted from the light-emitting location and scattered from (or in the case of fluorescence, emitted from) a sample of interest. For example, in some embodiments, the photodetector is displaced from the light emitting location (e.g., the distal end of the optical fiber) by a distance of no greater than about 10 mm (as measured by the shortest distance between the light-emitting location and the photodetector). This includes embodiments in which the photodetector is displaced from the light emitting location by a distance of no greater than about 2 mm and further includes embodiments in which the photodetector is displaced from the light emitting location by a distance of no greater than about 0.5 mm. However, the photodetectors are desirably located sufficiently far from the light-emitting location, or are shielded from the light-emitting location, in order to avoid or minimize light from the optical fiber directly impinging upon the photodetector.

In some embodiments of the present fiber optic probes, each light-emitting location will have at least one photodetector in the vicinity thereof. In some embodiments, one or more of the light-emitting locations will have a plurality of photodetectors (e.g., two) in the vicinity thereof. In some embodiments, a single photodetector can be in the vicinity of more than one light-emitting location. Advantages to using multiple photodetectors include improving the statistical acquisition of data, providing directionality to the detection of scattered or fluorescing light and correcting for changes in the spectral response of individual detectors. In addition, a fiber optic probe design that takes advantage of multiple light-emission locations and photodetectors can simultaneously probe a larger volume of a given sample. FIG. 2(b) shows a schematic diagram of a cross-section of the optical fiber of FIG. 2(a) having two photodetectors 208, 210 in the vicinity of light-emitting locations 204, 206.

Figure 3:
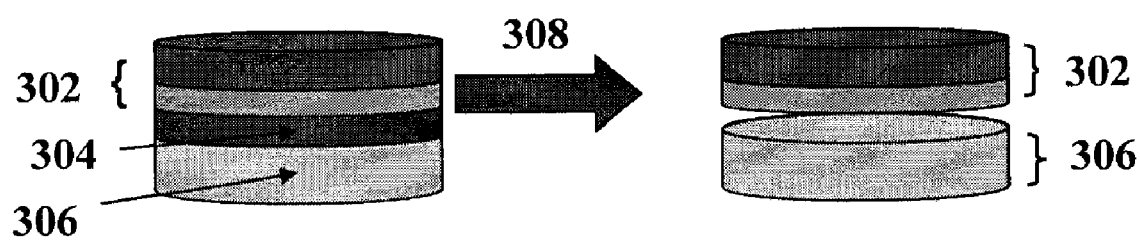
FIG. 3 illustrates a method of forming the photodetector device layers of a thin, flexible photodetector.

One embodiment of a method for forming the photodetector device layers of a fiber optic probe in accordance with the present invention is depicted in FIG. 3. In this method, the device layers of photodetector 302 are grown (e.g., using epitaxial growth techniques) on a sacrificial support layer 304 that is selectively etchable. The sacrificial layer can be supported by an underlying substrate, such as a wafer 306. This sacrificial support can be an AlAs layer or an InGaP layer in the case of GaAs-based device layers. This sacrificial support can then be etched away 308 with an appropriate etchant to release the device layer of the photodetector. For example, AlAs and InGaP can be etched in HCl which does not etch GaAs. The device layers are preferably grown in a lattice-matched or strain-free condition in order to prevent the curling of the thin layers after release. In some embodiments, the device layers form a p-i-n diode structure comprising heavily doped n and p layers in order to facilitate electrical contact. The device layer can also take the form of a MSM (metal-semiconductor-metal) structures and a Schottky barrier diode.

Figure 4:
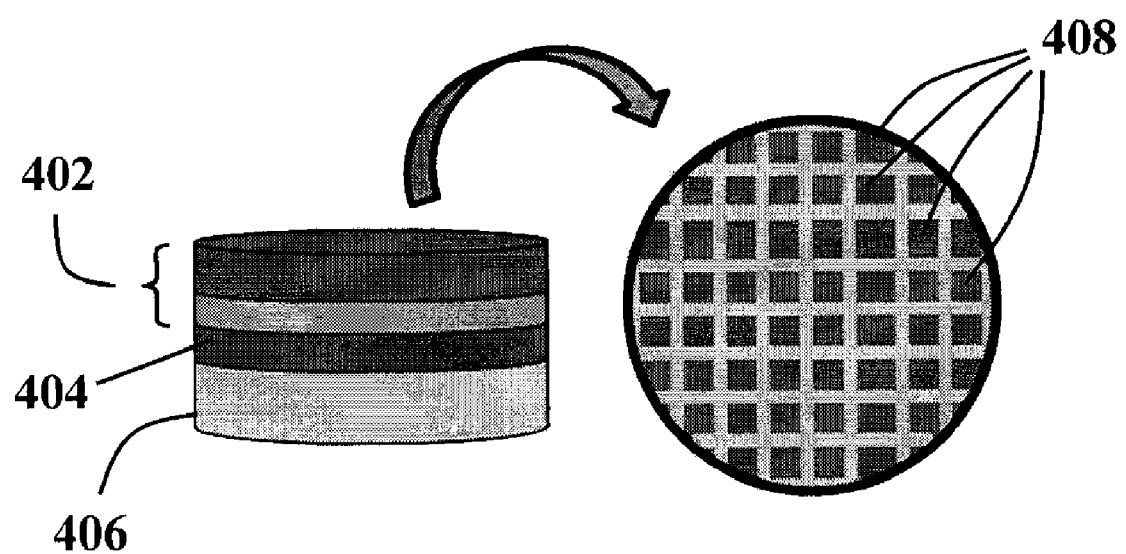
FIG. 4 illustrates part of a method of forming a plurality of photodetector device units on a substrate wafer.

One illustrative sequence for forming a plurality of photodiode device layers on a wafer can be carried out as follows. As shown in FIG. 4, device layers 402 grown on a wafer 406 can be non-selectively etched to form a plurality of individual photodetector device units 408. This can be accomplished by etching down to the substrate using standard lithographic techniques. After the individual photodetector device units have been defined, the exposed upper surface of the device units can be coated with a flexible polymer such as, but not limited to, benzocyclobutene (BCB), polymethyl methacrylate (PMMA), the epoxy-based photoresist SU-8, or polydimethyl siloxane (PDMS). All of these materials are semiconductor-compatible polymers which have reasonable adherence to device layers and can serve as an intermediary support for the released photodetector device units for subsequent handling and transfer. Once coated with the handling polymer, the underlying wafer substrate, including the sacrificial support layer 404, can be lapped to remove most of the substrate. The remainder of the substrate can be removed through chemical etching. The now-exposed backsides of the photodetector device units can be metalized with a thin compliant metal such as a <20 nm think layer of Au in order to facilitate bonding of the units to the electrical contacts on the optical fiber. Alternatively, the photodetector device units can be released from the substrate after pixilation and left suspended in the etch medium. Typically, these thin device units will reside on the surface of the aqueous etch solution due to the high surface tension until they are ready for transfer and bonding to the optical fiber.

Once the device units have been fabricated and released from the substrate, they can be mounted on an optical fiber. Owing to their thin structure, they will adhere to and conform to the external surface of the fiber. The gold-to-gold contact, using the embodiment discussed above, makes ready contact under modest or no pressure. Once the device units are affixed to the fiber, the polymer handing layer can be removed using an appropriate solvent, leaving the photodetectors on the surface of the optical fiber. The assembly (i.e., the photodetectors and metalized optical fiber) then can be coated with a transparent dielectric, such as $SiO_2$ or a thin film polymer layer. Top electrical contacts can be made through openings in the dielectric layer using a transparent oxide or thin metallization with or without patterning. The dielectric coating serves to isolate the two electrical leads. The contact to the leads at the end of the fiber can be made with conventional fiber mounting.

What is claimed is:

1. An apparatus comprising:
   (a) light source;
   (b) an optical fiber having a distal end, a proximal end and a side-wall, the proximal end in optical communication with the light source, wherein the optical fiber is configured to emit light from its distal end, at least one location along its side-wall, or both;
   (c) at least one photodetector having a device layer bonded to and conforming to the curvature of the curved outer surface of the side-wall of the optical fiber, wherein the at least one photodetector is positioned such that light from the optical fiber will not directly impinge upon the at least one photodetector; and
   (d) an electrically conductive lead in electrical communication with at least one photodetector.

2. An apparatus comprising:
   (a) an optical fiber;
   (b) at least one photodetector having a device layer bonded to and conforming to the curvature of the curved outer surface of the side-wall of the optical fiber;
   (c) an electrically conductive lead in electrical communication with at least one photodetector; and
   (d) a layer of electrically conductive material disposed between the optical fiber and at least one photodetector, wherein the layer of electrically conductive material provides a back electrode for the at least one photodetector.

3. The apparatus of claim 1, further comprising a layer of dielectric material coating a portion of the photodetector.

4. The apparatus of claim 1, wherein the at least one photodetector is located no more than 10 mm from the distal end of the optical fiber.

5. The apparatus of claim 1, wherein the optical fiber is configured to emit light from its distal end and from at least one additional location along its side-wall, the apparatus further comprising at least one additional photodetector having a device layer bonded to and conforming to the curvature of the curved outer surface of the side-wall of the optical fiber in the vicinity of the at least one additional light-emitting location.

6. The apparatus of claim 1, comprising a plurality of photodetectors disposed around the circumference of the optical fiber, wherein each of the plurality of photodetectors is bonded to and conforms to the curvature of the curved outer surface of the side-wall of the optical fiber.

7. The apparatus of claim 6, wherein the optical fiber is configured to emit light at a plurality of locations around its circumference, and further wherein at least one of the plurality of photodetectors is located in the vicinity of each of the plurality of light-emitting locations.

8. The apparatus of claim 1, further comprising a biopsy needle containing the optical fiber.

9. A method for using the apparatus of claim 1, the method comprising:
   (a) placing the optical fiber in close proximity to a sample; and
   (b) emitting light from the optical fiber;
   wherein return light from the sample is detected by the at least one photodetector via absorption of said return light by the photodetector.

10. The method of claim 9, wherein the sample comprises a biologic tissue.

11. The method of claim 10, wherein the optical fiber is contained in a biopsy needle and placing the optical fiber in close proximity to the sample comprises inserting the biopsy needle into the biological tissue.

12. The method of claim 10, further comprising using the detected return light to measure the wavelength-dependent absorbance characteristics of hemoglobin in the biological tissue sample.

13. The method of claim 9, wherein the return light is absorbed by the at least one photodetector in vivo.

14. The method of claim 9, wherein the return light is light scattered from the sample.

15. The method of claim 9, wherein the sample comprises a chromophore and the return light is florescence emitted from the sample.

16. The apparatus of claim 1, wherein the radius of curvature of the device layer bonded to and conforming to the curvature of the curved outer surface of the side-wall of the optical fiber is greater than the thickness of the device layer.

17. The apparatus of claim 1, wherein the at least one photodetector is located no more than 2 mm from the distal end of the optical fiber.

18. The apparatus of claim 16, wherein the at least one photodetector comprises device layers having a thickness of no greater than about 10 µm.

19. The apparatus of claim 18, wherein the at least one photodetector is a thin film semiconductor photodetector having direct-bandgap semiconductor-based device layers.

20. The apparatus of claim 2, wherein the at least one photodetector is further positioned such that reflected or fluorescent return light from the sample in close proximity to the optical fiber will be detected by the photodetector via absorption of said return light by the photodetector.

* * * * *